(12) United States Patent
Manderfeld et al.

(10) Patent No.: US 10,046,146 B2
(45) Date of Patent: *Aug. 14, 2018

(54) CUTTING BALLOON CATHETER

(71) Applicant: BOSTON SCIENTIFIC SCIMED, INC., Maple Grove, MN (US)

(72) Inventors: Chris Manderfeld, St. Michael, MN (US); James Q. Feng, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/056,304

(22) Filed: Feb. 29, 2016

(65) Prior Publication Data

US 2016/0175568 A1 Jun. 23, 2016

Related U.S. Application Data

(63) Continuation of application No. 13/944,039, filed on Jul. 17, 2013, now Pat. No. 9,302,071, which is a
(Continued)

(51) Int. Cl.
*B29C 65/48* (2006.01)
*A61M 25/10* (2013.01)
(Continued)

(52) U.S. Cl.
CPC . *A61M 25/1027* (2013.01); *A61B 17/320725* (2013.01); *A61M 25/0009* (2013.01);
(Continued)

(58) Field of Classification Search
CPC .... A61M 2025/1031; A61M 2025/109; A61B 17/320725; B29C 39/10
See application file for complete search history.

(56) References Cited

U.S. PATENT DOCUMENTS 5,196,024 A 3/1993 Barath
5,209,799 A * 5/1993 Vigil .............. A61B 17/320725
156/156

(Continued)

OTHER PUBLICATIONS

Henkel North America, "Loctite® Brand Equipment-Light Curing Equipment & Meters", available on-line at https://web.archive.org/web/20091012193345/http://equipment.loctite.com/productLineDetail.cfm?pl=19, 3 pages, Oct. 2009.

(Continued)

*Primary Examiner* — William P Bell
(74) *Attorney, Agent, or Firm* — Seager, Tufte & Wickhem LLP

(57) ABSTRACT

A medical balloon catheter including a catheter shaft and an inflatable balloon secured to a distal portion of the catheter shaft. One or more cutting blades are secured to the inflatable balloon by a first polymeric adhesive material forming a mounting pad encasing a base portion of the cutting blade therein, and a second polymeric adhesive material adhesively bonding the mounting pad to a surface of the balloon. The first polymeric adhesive material has a first ductility and the second polymeric adhesive material has a second ductility greater than the first ductility.

13 Claims, 14 Drawing Sheets

Related U.S. Application Data continuation of application No. 13/336,654, filed on Dec. 23, 2011, now Pat. No. 8,491,615.

(60) Provisional application No. 61/428,107, filed on Dec. 29, 2010.

(51) Int. Cl.
*A61B 17/3207* (2006.01)
*A61M 25/00* (2006.01)
*A61B 17/22* (2006.01)

(52) U.S. Cl.
CPC .... *B29C 65/48* (2013.01); *A61B 2017/22061* (2013.01); *A61M 2025/1031* (2013.01)

(56) References Cited

U.S. PATENT DOCUMENTS

| | | |
|---|---|---|
| 5,320,634 A | 6/1994 | Vigil et al. |
| 5,616,149 A | 4/1997 | Barath |
| 5,961,498 A | 10/1999 | Wiesendanger |
| 6,500,186 B2 | 12/2002 | Lafontaine et al. |
| 6,562,062 B2 | 5/2003 | Jenusaitis et al. |
| 6,632,231 B2 | 10/2003 | Radisch, Jr. |
| 6,680,767 B2 * | 1/2004 | Coates ............ B29C 33/68 349/117 |
| 6,746,463 B1 | 6/2004 | Schwartz |
| 6,808,531 B2 | 10/2004 | Lafontaine et al. |
| 6,951,566 B2 | 10/2005 | Lary |
| 7,011,670 B2 | 3/2006 | Radisch, Jr. |
| 7,029,483 B2 | 4/2006 | Schwartz |
| 7,153,315 B2 | 12/2006 | Miller |
| 7,172,609 B2 | 2/2007 | Radisch, Jr. |
| 7,291,158 B2 | 11/2007 | Crow et al. |
| 7,338,463 B2 | 3/2008 | Vigil |
| 7,413,558 B2 | 8/2008 | Kelley et al. |
| 7,494,497 B2 | 2/2009 | Weber |
| 7,771,447 B2 | 8/2010 | Kunis |
| 7,799,043 B2 | 9/2010 | O'Brien et al. |
| 8,038,691 B2 | 10/2011 | Bence et al. |
| 8,043,311 B2 | 10/2011 | Radisch, Jr. et al. |
| 2002/0010489 A1 | 1/2002 | Grayzel et al. |
| 2002/0169413 A1 | 11/2002 | Keren et al. |
| 2003/0163148 A1 | 8/2003 | Wang et al. |
| 2004/0133223 A1 | 7/2004 | Weber |
| 2005/0070888 A1 | 3/2005 | Dimatteo et al. |
| 2005/0119678 A1 | 6/2005 | O'Brien et al. |
| 2005/0137615 A1 | 6/2005 | Mapes et al. |
| 2005/0137616 A1 | 6/2005 | Vigil |
| 2005/0149102 A1 | 7/2005 | Radisch, Jr. et al. |
| 2005/0228343 A1 | 10/2005 | Kelley |
| 2005/0240148 A1 | 10/2005 | Cheves et al. |
| 2005/0245864 A1 | 11/2005 | O'Brien et al. |
| 2005/0288629 A1 | 12/2005 | Kunis |
| 2006/0106412 A1 | 5/2006 | Crow et al. |
| 2006/0106413 A1 | 5/2006 | Bence et al. |
| 2006/0111736 A1 | 5/2006 | Kelley |
| 2006/0116700 A1 | 6/2006 | Crow |
| 2006/0116701 A1 | 6/2006 | Crow |
| 2006/0129093 A1 | 6/2006 | Jackson |
| 2006/0135980 A1 | 6/2006 | Trinidad |
| 2006/0247674 A1 | 11/2006 | Roman |
| 2007/0016232 A1 | 1/2007 | St. Martin et al. |
| 2007/0060863 A1 | 3/2007 | Goeken et al. |
| 2007/0213752 A1 | 9/2007 | Goodin et al. |
| 2009/0171284 A1 | 7/2009 | Burke et al. |
| 2010/0204565 A1 | 8/2010 | Falkén et al. |
| 2010/0312264 A1 | 12/2010 | O'Brien et al. |

OTHER PUBLICATIONS

Loctite 3321, Henkel Technical Data Sheet, 3 pages, Jan. 2008.
Loctite 3943, Henkel Technical Data Sheet, 3 pages, May 2008.

* cited by examiner

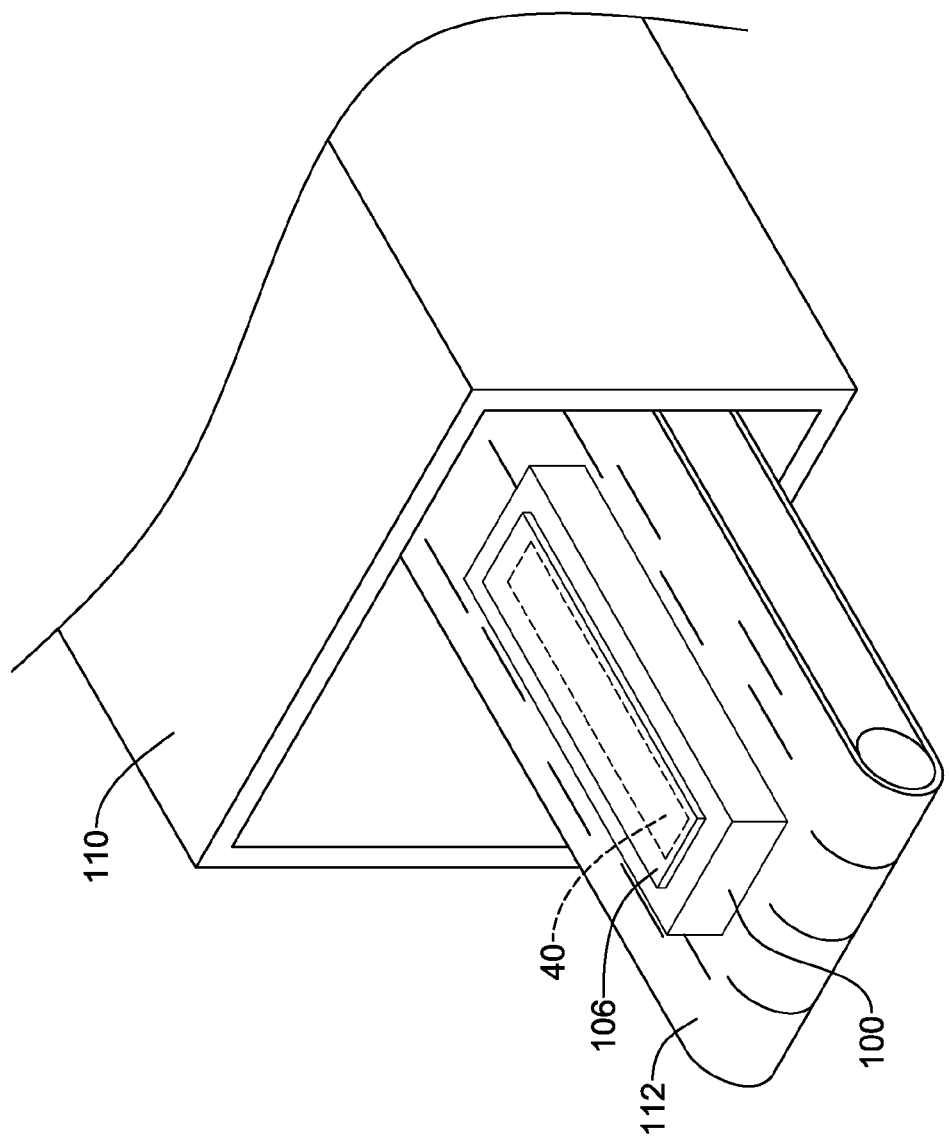

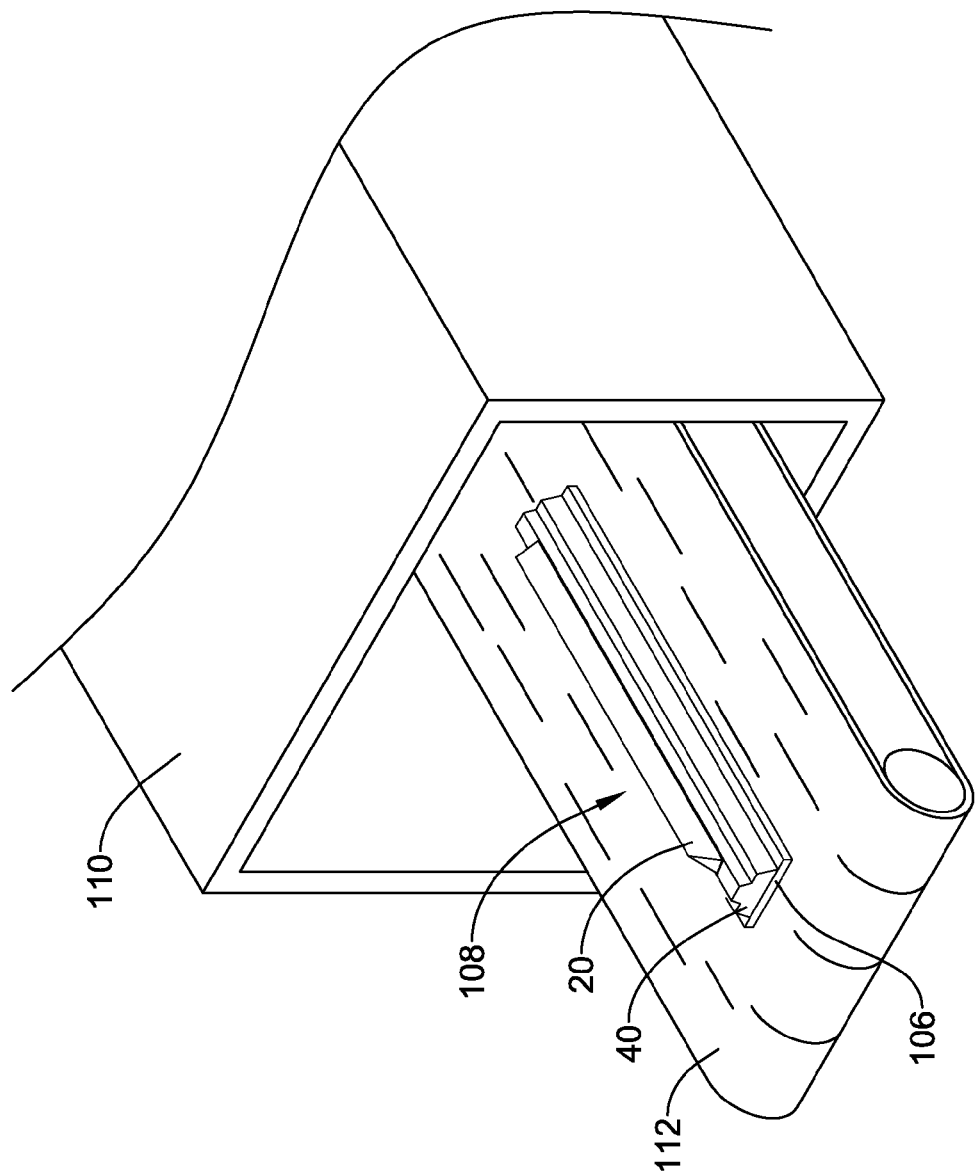

CUTTING BALLOON CATHETER

CROSS-REFERENCE TO RELATED APPLICATIONS

This application is a continuation of U.S. patent application Ser. No. 13/944,039, filed Jul. 17, 2013, which is a continuation of U.S. patent application Ser. No. 13/336,654, filed Dec. 23, 2011, now U.S. Pat. No. 8,491,615, which claims priority to U.S. Provisional Patent Application No. 61/428,107, filed on Dec. 29, 2010, the entire disclosures of which are incorporated herein by reference.

TECHNICAL FIELD

The disclosure pertains to angioplasty balloon catheters having cutting elements mounted onto an angioplasty balloon. More particularly, the disclosure is directed to adhesively bonding cutting blades to an angioplasty balloon.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened.

One of the major obstacles in treating coronary artery disease and/or treating blocked blood vessels is re-stenosis. Evidence has shown that cutting or scoring the stenosis, for example, with an angioplasty balloon equipped with a cutting element, during treatment can reduce incidence of re-stenosis. Additionally, cutting or scoring the stenosis may reduce trauma at the treatment site and/or may reduce the trauma to adjacent healthy tissue. Cutting elements may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting elements having cutting edges have been developed to attempt to enhance angioplasty treatments. There is an ongoing need for improved structures and methods of mounting cutting elements, such as cutting blades onto an inflatable angioplasty balloon of an angioplasty balloon catheter.

SUMMARY

The disclosure is directed to several alternative designs, materials and methods of manufacturing medical device structures and assemblies.

Accordingly, one illustrative embodiment is a medical balloon catheter including a catheter shaft and an inflatable balloon secured to a distal portion of the catheter shaft. At least one cutting blade is secured to the inflatable balloon by a first polymeric adhesive material forming a mounting pad encasing a base portion of the cutting blade therein, and a second polymeric adhesive material adhesively bonding the mounting pad to a surface of the balloon. The first polymeric adhesive material has a first ductility and the second polymeric adhesive material has a second ductility greater than the first ductility.

Another illustrative embodiment is a medical balloon catheter including a catheter shaft and an inflatable balloon secured to a distal portion of the catheter shaft. The catheter shaft includes an inflation lumen in fluid communication with the inflatable balloon. A cutting blade including a cutting edge and a base portion opposite the cutting edge is mounted to the balloon by a first polymeric adhesive material forming a mounting pad encasing the base portion of the cutting blade therein, and a second polymeric adhesive material adhesively bonding the mounting pad to a surface of the balloon. The mounting pad includes a bottom surface and first and second opposing side surfaces. A first portion of the second polymeric adhesive material is interposed between the bottom surface of the mounting pad and the surface of the balloon, and second and third portions of the second polymeric adhesive material contact the first and second opposing side surfaces of the mounting pad, respectively.

Yet another illustrative embodiment is a method of securing a cutting blade to a balloon of a balloon catheter. The method includes molding a mounting pad formed of a first polymeric adhesive material about a base portion of a cutting blade, such that base portion of the cutting blade is encased in the mounting pad. The mounting pad, with the base portion of the cutting blade encased therein, is then adhered to a surface of a balloon with a second polymeric adhesive material having a ductility greater than the first polymeric adhesive material.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
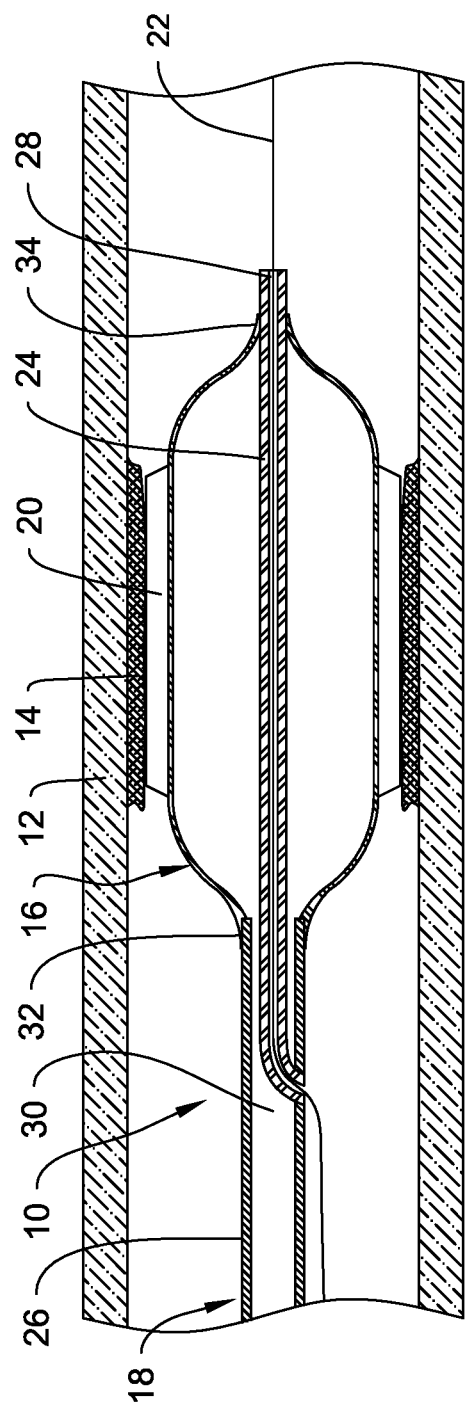
FIG. 1 is a partial cross-sectional side view of an exemplary cutting balloon catheter disposed in a blood vessel.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "ductility" refers to the ability of a material to be plastically deformed by elongation without fracture. Ductility of a material is typically measured as a percentage increase in length at fracture compared with its original length and is termed percent elongation.

As used in this specification and the appended claims, the term "lower" refers to a portion facing toward the central longitudinal axis and the term "upper" refers to a portion facing away from the central longitudinal axis.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

FIG. 1 is a partial cross-sectional side view of an example catheter 10 disposed in a blood vessel 12 and positioned adjacent an intravascular lesion 14. The catheter 10 may include a balloon 16 coupled to a catheter shaft 18. One or more cutting members or blades 20 may be mounted on the balloon 16. In general, the catheter 10 may be advanced over a guidewire 22, through the vasculature, to a target area. Once positioned at the target location in the vasculature, the balloon 16 can be inflated to exert a radially outward force on the lesion 14, as the cutting members 20 engage the lesion 14. Thus, the cutting members 20 may cut or score the lesion 14 to facilitate enlarging the lumen proximate the lesion 14. The target area may be within any suitable peripheral or cardiac vessel lumen location.

The cutting members 20 may vary in number, position, and arrangement about the balloon 16. For example, the catheter 10 may include one, two, three, four, five, six, or more cutting members 20 that are disposed at any position along the balloon 16 and in a regular, irregular, or any other suitable pattern. For example, in some embodiments the balloon 16 may include a plurality of cutting members 20 longitudinally arranged symmetrically around the circumference of the balloon 16.

The cutting members 20 may be made from any suitable material such as a metal, metal alloy, polymer, metal-polymer composite, and the like, or any other suitable material. For example, cutting members 20 may be made from stainless steel, titanium, nickel-titanium alloys, tantalum, iron-cobalt-nickel alloys, or other metallic materials in some instances.

The balloon 16 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyetherester, polyester, polyamide, elastomeric polyamides, polyether block amide (PEBA), as well as other suitable materials, or mixtures, combinations, copolymers thereof, polymer/metal composites, and the like.

The balloon 16 may be configured so that the balloon 16 includes one or more "wings" or wing-shaped regions when the balloon 16 is deflated. In some instances, the wings may be configured so that the cutting members 20 can be positioned at the inward-most positions of the deflated balloon 16, with cutting members 20 enfolded under the wings of the balloon 16. This arrangement may reduce the exposure of the cutting members 20 to the blood vessel during delivery of the balloon 16 to the lesion 14.

The shaft 18 may be a catheter shaft, similar to typical catheter shafts. For example, the catheter shaft 18 may include an outer tubular member 26 and an inner tubular member 24 extending through at least a portion of the outer tubular member 26. Tubular members 24/26 may be manufactured from a number of different materials. For example, tubular members 24/26 may be made of metals, metal alloys, polymers, metal-polymer composites or any other suitable materials.

Tubular members 24/26 may be arranged in any appropriate way. For example, in some embodiments the inner tubular member 24 can be disposed coaxially within the outer tubular member 26. According to these embodiments, the inner and outer tubular members 24/26 may or may not be secured to one another along the general longitudinal axis of the catheter shaft 18. Alternatively, the inner tubular member 24 may follow the inner wall or otherwise be disposed adjacent the inner wall of the outer tubular member 26. In other embodiments, the tubular members 24/26 may be arranged in another desired fashion.

The inner tubular member 24 may include an inner lumen 28. In at least some embodiments, the inner lumen 28 is a guidewire lumen for receiving the guidewire 22 therethrough. Accordingly, the catheter 10 can be advanced over the guidewire 22 to the desired location. The guidewire lumen 28 may extend along essentially the entire length of the catheter shaft 18 such that catheter 10 resembles traditional "over-the-wire" catheters. Alternatively, the guidewire lumen 28 may extend along only a portion of the catheter shaft 18 such that the catheter 10 resembles "single-operator-exchange" or "rapid-exchange" catheters.

The catheter shaft 18 may also include an inflation lumen 30 that may be used, for example, to transport inflation media to and from the balloon 16 to selectively inflate and/or deflate the balloon 16. The location and position of the inflation lumen 30 may vary, depending on the configuration of the tubular members 24/26. For example, when the outer tubular member 26 surrounds the inner tubular member 24, the inflation lumen 30 may be defined within the space between the tubular members 24/26. In embodiments in which the outer tubular member 26 is disposed alongside the inner tubular member 24, then the inflation lumen 30 may be the lumen of the outer tubular member 26.

The balloon 16 may be coupled to the catheter shaft 18 in any of a number of suitable ways. For example, the balloon 16 may be adhesively or thermally bonded to the catheter shaft 18. In some embodiments, a proximal waist 32 of the balloon 16 may be bonded to the catheter shaft 18, for example, bonded to the distal end of the outer tubular member 26, and a distal waist 34 of the balloon 16 may be bonded to the catheter shaft 18, for example, bonded to the distal end of the inner tubular member 24. The exact bonding positions, however, may vary.

Figure 2:
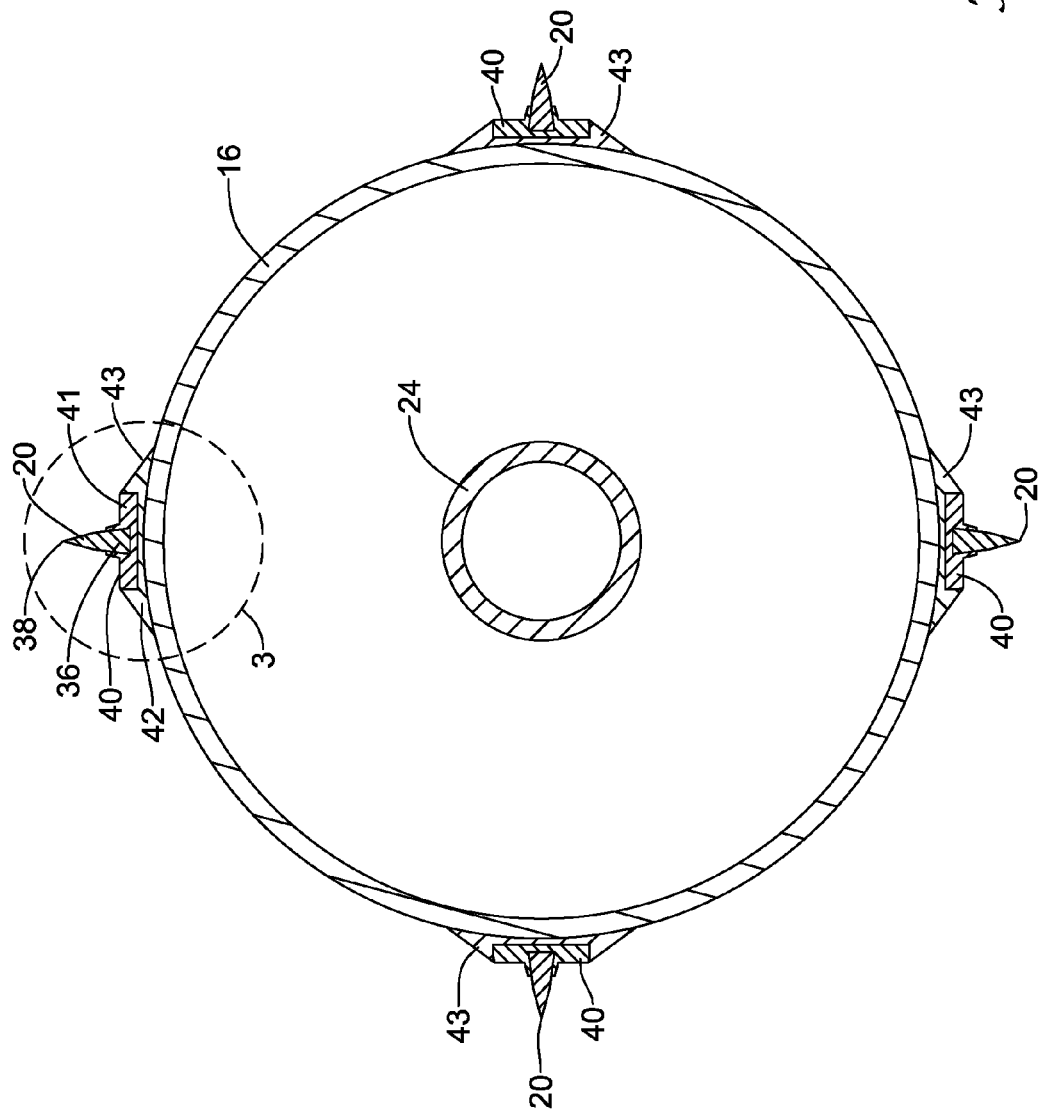
FIG. 2 is a transverse cross-sectional view of an inflatable balloon of a balloon catheter having a plurality of cutting elements mounted thereon.

FIG. 2 is a transverse cross-sectional view showing one possible arrangement of cutting members or blades 20 mounted to the balloon 16. While the balloon 16 is shown having four cutting members 20 mounted thereon, in other embodiments, the balloon 16 may include one, two, three, five, six, seven, eight, or more cutting members 20. The cutting members 20 may be symmetrically or asymmetrically spaced around the circumference of the balloon 16. The cutting members 20 may include a base portion 36 and a cutting edge 38 opposite the base portion 36 extending radially outward from the balloon 16.

The cutting members 20 may be secured to the outer surface of the balloon 16 by encasing the base portion 36 of the cutting member 20 in a mounting pad 40 formed of a first polymeric adhesive material 41, and adhesively bonding the mounting pad 40, with the base portion 36 of the cutting member 20 embedded therein, to the outer surface of the balloon 16 with a second polymeric adhesive material 42 forming a base 43. Accordingly, FIGS. 3-6 illustrate some exemplary embodiments of mounting a cutting member 20 to the balloon 16.

The first polymeric adhesive material 41 may be a high tensile strength, UV cured, medical grade adhesive with low ductility. For example, the first polymeric adhesive material 41 may have a tensile strength of about 2,500 psi or more, about 3,000 psi or more, or about 3,500 psi or more. Furthermore, the percent elongation at break of the first polymeric adhesive material 41 may be about 12% or less, about 10% or less, or about 8% or less. For example, the percent elongation at break of the first polymeric adhesive material 41 may be about 5% to about 10%, or about 6% to about 7% in some instances. One suitable ultraviolet (UV) light curable polymeric adhesive material to use as the first polymeric adhesive material 41 is Loctite® 3943.

The second polymeric adhesive material 42 may be a relatively high tensile strength, UV cured, medical grade adhesive with high ductility. For example, the second polymeric adhesive material 42 may have a tensile strength of about 2,500 psi or more, about 3,000 psi or more, or about 3,500 psi or more. The ductility of the second polymeric adhesive material 42 may be greater than the ductility of the first polymeric adhesive material 41. For example, the percent elongation at break of the second polymeric adhesive material 42 may be about 10 times or more, about 15 times or more, about 20 times or more, about 25 times or more, about 30 times or more, or about 35 times or more the percent elongation at break of the first polymeric adhesive material 41. For example, the percent elongation at break of the second polymeric adhesive material 42 may be about 100% or more, about 150% or more, about 200% or more, about 225% or more, or about 250% or more. Thus, the second polymeric adhesive material 42 may be softer or more flexible than the first polymeric adhesive material 41 (which may be harder or more rigid than the second polymeric adhesive material 41). One suitable ultraviolet (UV) light curable polymeric adhesive material for use as the second polymeric adhesive material 42 is Loctite® 3321.

The combination of components used in the sub-assembly to secure the cutting member 20 to the balloon 16 may be chosen to provide specific structural characteristics. For example, the first polymeric adhesive material 41, forming the mounting pad 40, may secure the cutting member 20, while the second polymeric adhesive material 42, forming the base 43, may readily adhere to the material of the balloon 16 and more closely match the radial and longitudinal growth of the balloon 16 through inflation. For instance, the outside diameter of the balloon 16 may increase by 4% or more, 6% or more, 8% or more, or 10% or more when inflated to its rated burst pressure during use. Thus, it may be desirable to select the second polymeric adhesive material 42 which has a percent elongation at break which is greater than or equal to the percent of radial growth of the balloon 16 when expanded to its rated burst pressure (e.g., 10 ATM, 12 ATM, 15 ATM) to ensure that the base 43 has sufficient ductility to stretch in accordance with the expansion of the balloon 16 when the balloon 16 is inflated. For example, a second polymeric adhesive material 42 having a percent elongation at break of greater than 12% may be chosen in some embodiments.

Figure 3:
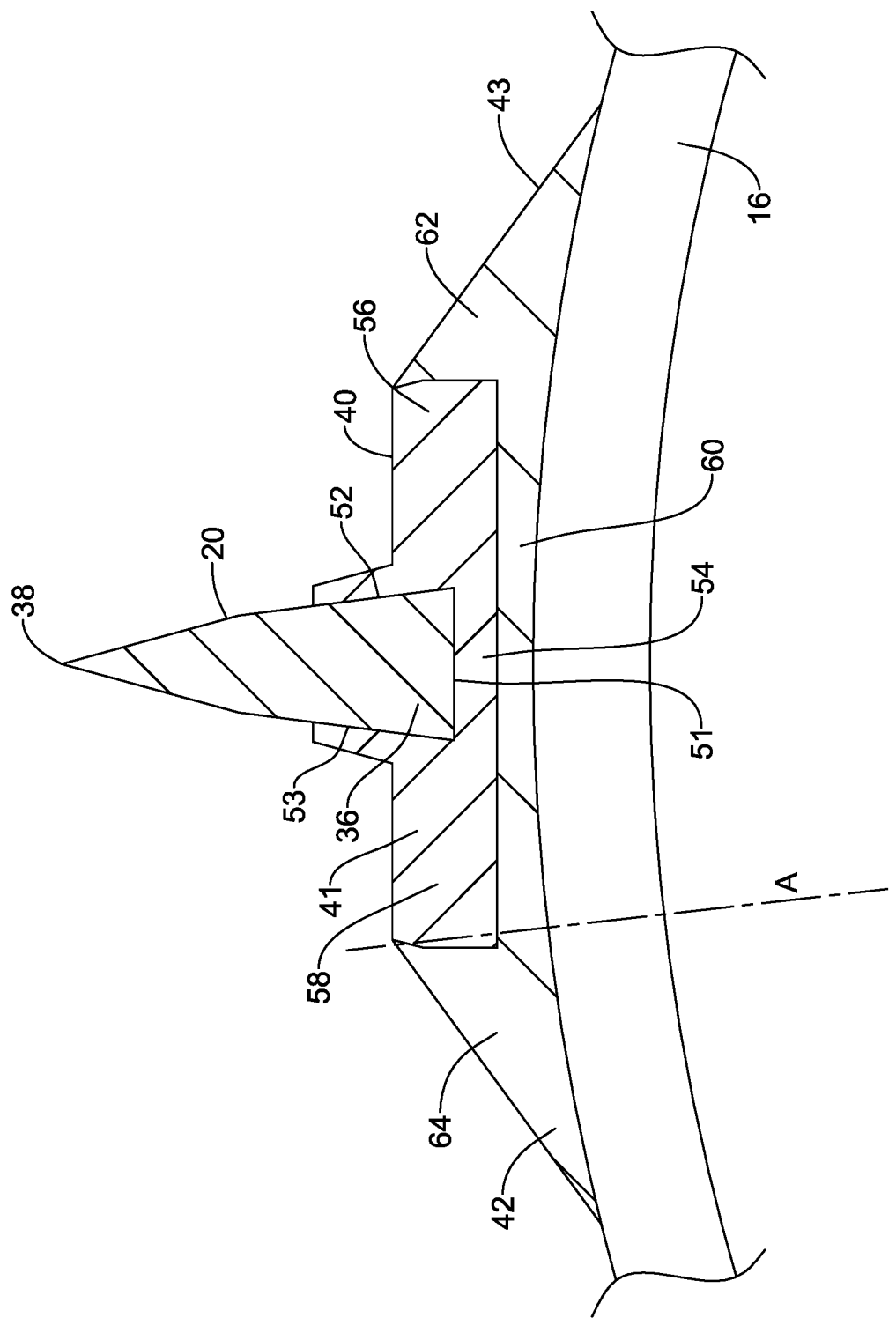
FIG. 3 is a cross-sectional view of an exemplary arrangement of a cutting element mounted to a balloon of a balloon catheter.

In one embodiment, shown in FIG. 3, the base portion 36 of the cutting member 20 may be embedded in the mounting pad 40 of the first polymeric adhesive material 41 such that the first polymeric adhesive material 41 is in contact with the lower surface 51, a first side surface 52, and a second side surface 53 of the cutting member 20. Thus, the mounting pad 40 may include a base portion 54 radially inward of the lower surface 51 and first and second opposing wing portions 56, 58 extending circumferentially from the first and second side surfaces 52, 53, respectively. Although not shown in FIG. 3, the first polymeric adhesive material 41 may extend through openings 50 in the base portion 36 (described further with respect to FIGS. 7 and 8) from the first side surface 52 to the second side surface 53 to help mechanically interlock the mounting pad 40 to the cutting member 20.

The base 43 formed of the second polymeric adhesive material 42 may be adhesively bonded to both a surface of the mounting pad 40 and the exterior surface of the balloon 16. For instance, the base 43 may include a layer 60 of the second polymeric adhesive material 42 interposed between the lower surface of the mounting pad 40 and the exterior surface of the balloon 16 and adhesively bonded thereto, and/or the base 43 may include first and second fillets 62, 64 of the second polymeric adhesive material 42 contacting and adhesively bonded to opposing side surfaces of the mounting pad 40 and the exterior surface of the balloon 16. In some instances, the fillets 62, 64 may include an angled surface angled at about 15°, about 30°, or about 45° to the lower surface of the base 43.

In some instances, as shown in FIG. 3, a portion of the fillets 62, 64 of the second polymeric adhesive material 42 may be located radially outward of the opposing wing portions 56, 58 of the first polymeric adhesive material 41 such that an imaginary line A extending radially outward from the central longitudinal axis of the balloon 16 passes through both the first polymeric adhesive material 41 and the portion of the second polymeric adhesive material 42 located radially outward of the first polymeric adhesive material 41. Such a configuration, in addition to the adhesive bond between the base 43 and the mounting pad 40, may mechanically interlock the mounting pad 40 in the base 43 to help strengthen the securement of the base 43 to the mounting pad 40.

Figure 4:
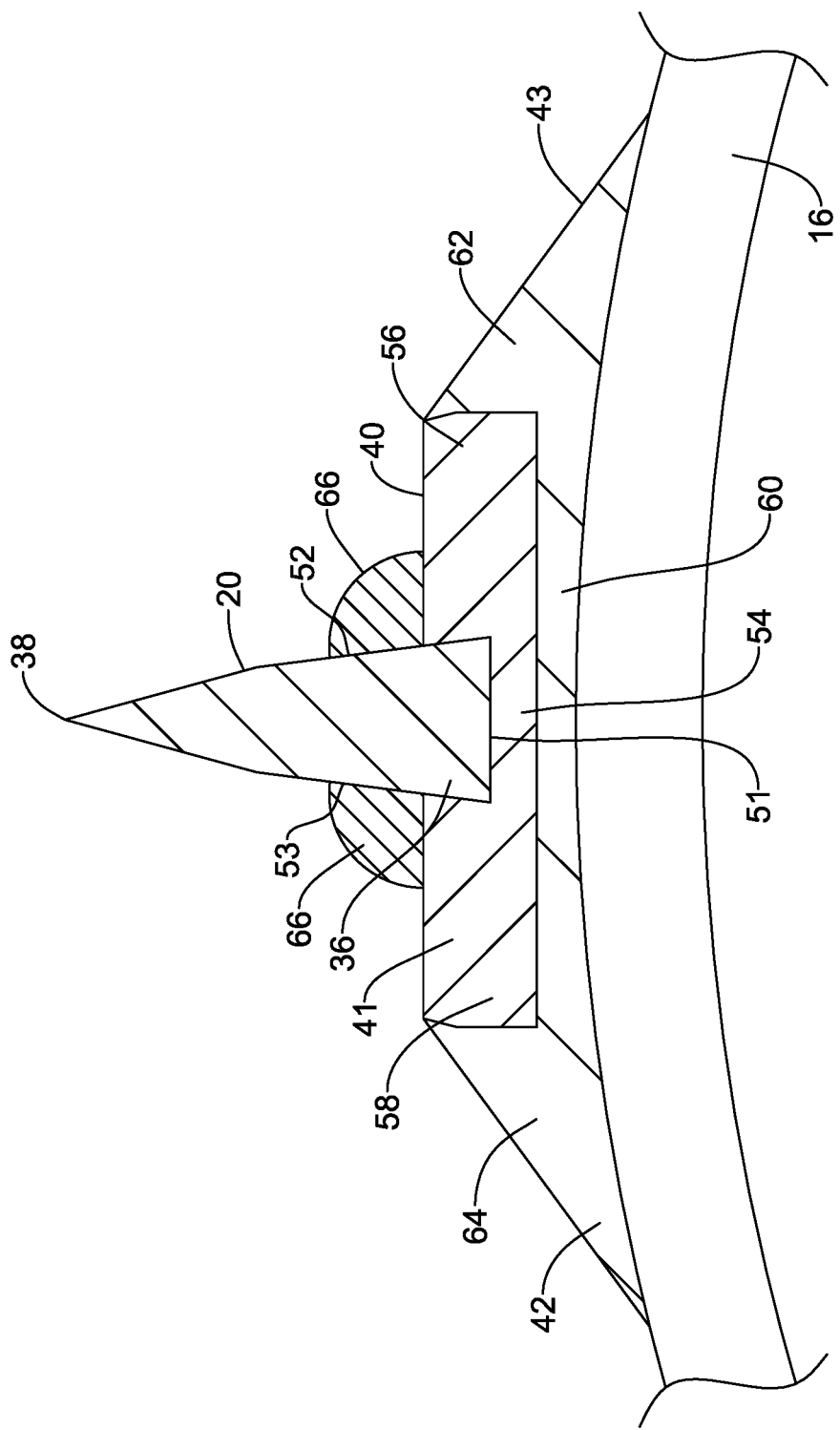
FIG. 4 is a cross-sectional view of another exemplary arrangement of a cutting element mounted to a balloon of a balloon catheter.

Another embodiment, shown in FIG. 4, may be similar to the embodiment shown in FIG. 3, with the inclusion of first and second reliefs 66 located on opposing side surfaces 52, 53, respectively. In some instances, the reliefs 66 may have a beveled, chamfered, or radiused edge extending between the cutting member 20 and one of the opposing wings 56, 58 of the mounting pad 40. Thus, the reliefs 66 may contact both the mounting pad 40 and the cutting member 20, providing a transition at the interface between the cutting member 20 and the wing portions 56, 58 of the mounting pad 40. The reliefs 66, which may extend the length of the cutting member 20, may be formed subsequent to casting the cutting member 20 in the mounting pad 40. The reliefs 66 may be formed of the second polymeric adhesive material 42, or another polymeric adhesive material if desired.

Figure 5:
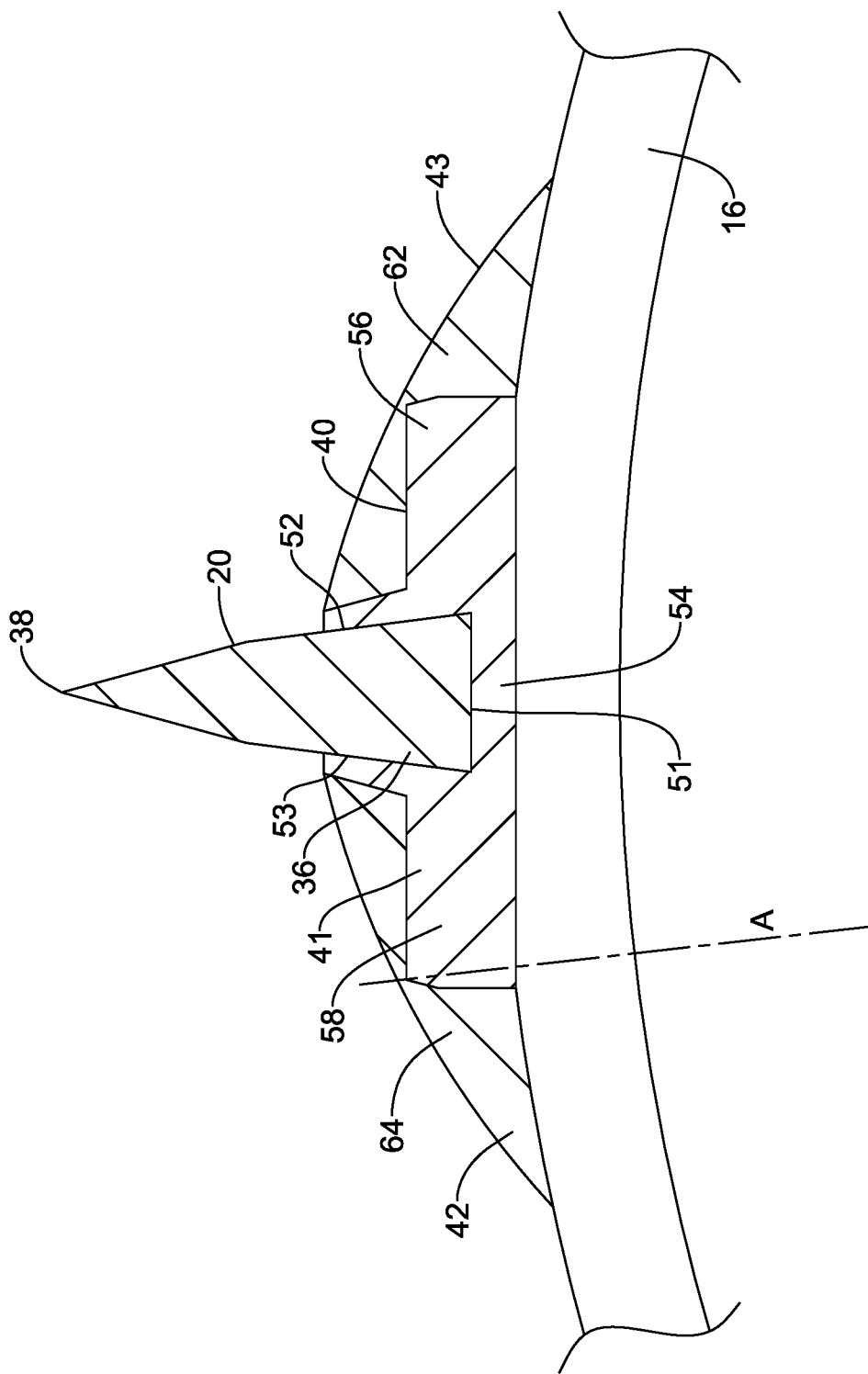
FIG. 5 is a cross-sectional view of another exemplary arrangement of a cutting element mounted to a balloon of a balloon catheter.

Another embodiment, shown in FIG. 5, may include a mounting pad 40 similar to the embodiment shown in FIG. 3. However, as shown in FIG. 5, the base 43 formed of the second polymeric adhesive material 42 may be provided on opposing sides of the cutting member 20 and the wing portions 56, 58 of the mounting pad 40 and covering the upper surface of the wing portions 56, 58. In such an embodiment, the base 43 may include first and second fillets 62, 64 of the second polymeric adhesive material 42 contacting and adhesively bonded to opposing side surfaces of the mounting pad 40 and the exterior surface of the balloon 16 including a portion of the fillets 62, 64 of the second polymeric adhesive material 42 located radially outward of the opposing wing portions 56, 58 of the first polymeric adhesive material 41 such that an imaginary line A extending radially outward from the central longitudinal axis of the balloon 16 passes through both the first polymeric adhesive material 41 and the portion of the second polymeric adhesive material 42 located radially outward of the first polymeric adhesive material 41. Such a configuration, in addition to the adhesive bond between the base 43 and the mounting pad 40, may mechanically interlock the mounting pad 40 in the base 43 to help strengthen the securement of the base 43 to the mounting pad 40. In some instances, the fillets 62, 64 may include an angled surface angled at about 15°, about 17.5°, about 25°, about 30°, or about 45° to the lower surface of the base 43. The base 43, shown in FIG. 5, may form a smooth, gradual transition overlaying the mounting pad 40 from the side surfaces 52, 53 of the cutting member 20 to the exterior surface of the balloon 16.

In the embodiment shown in FIG. 5, the lower surface of the mounting pad 40 is shown in direct contact with the exterior surface of the balloon 16. It is noted however that, although the embodiment shown in FIG. 5 does not include a layer of the second polymeric adhesive material 42 interposed between the lower surface of the mounting pad 40 and the exterior surface of the balloon 16, in some instances, a layer of the second polymeric adhesive material 42 may be included, similar to that shown in FIG. 3, interposed between the lower surface of the mounting pad 40 and the surface of the balloon 16.

Figure 6:
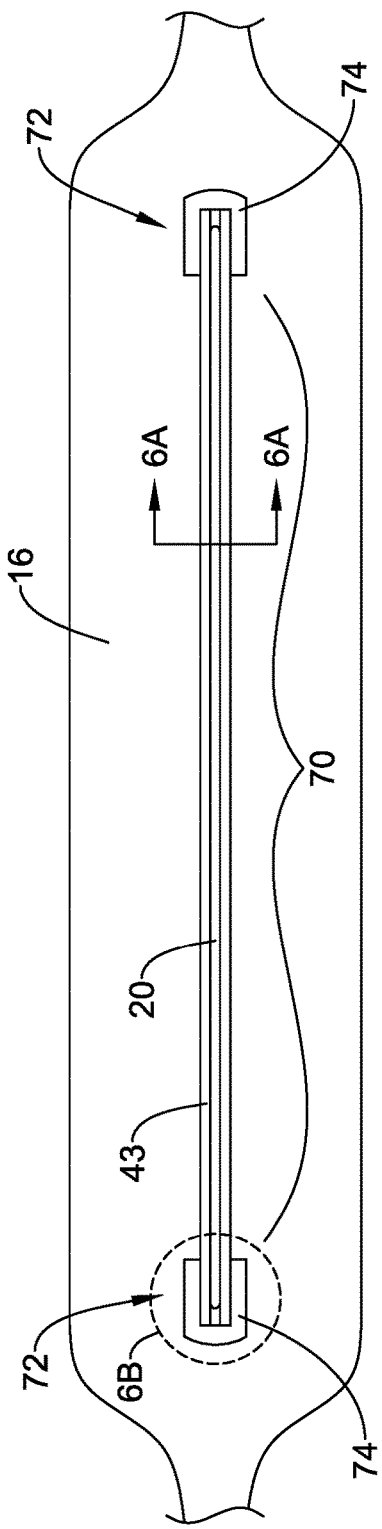
FIG. 6 is a top view of another exemplary arrangement of a cutting element mounted to a balloon of a balloon catheter.

FIG. 6 is a top view of another embodiment of a cutting member 20 adhesively mounted to the balloon 16. As shown in FIG. 6, the subassembly for securing the cutting member 20 to the balloon 16 may include opposing end portions 72 and an intermediate portion 70 extending between the opposing end portions 72. As shown by the cross-section of FIG. 6A, taken along line 6A-6A of FIG. 6, the intermediate portion 70 may resemble that of the cross-section of the embodiment shown in FIG. 5. In other instances, the cross-section of the intermediate portion 70 may resemble that of the cross-section of the embodiment shown in FIG. 3 or FIG. 4, for example.

The cutting member 20 may have a width W1, the mounting pad 40 may have a width W2 greater than the width W1 of the cutting member 20, and the base 43 may have a width W3 greater than the width W2 of the mounting pad 40. Width, as used herein, refers to the dimension transverse to the longitudinal axis of the cutting member 20.

Figure 6B:
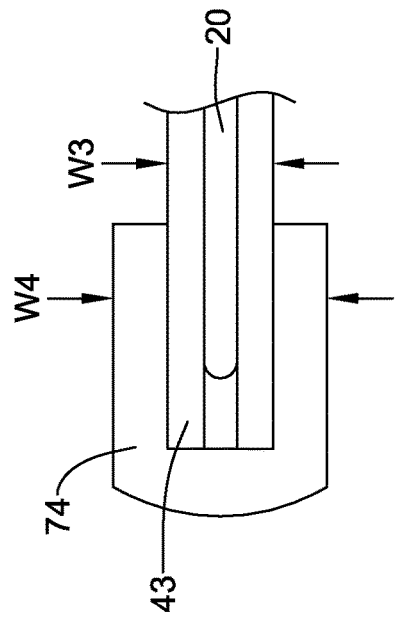
FIG. 6B is an enlarged top view of a portion of the arrangement of FIG. 6.
Figure 6A:
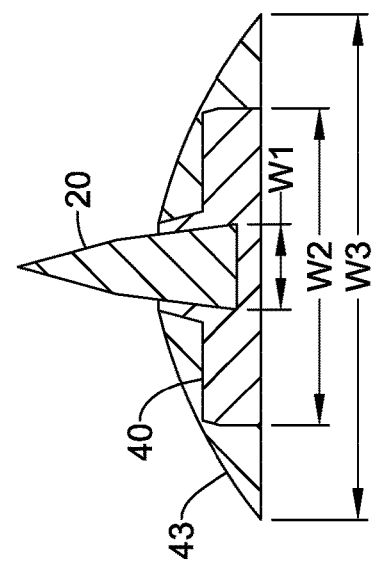
FIG. 6A is a cross-sectional view of the arrangement of FIG. 6 taken along line 6A-6A.

As shown in the enlarged view of FIG. 6B, an enlarged foot 74 formed of the second polymeric adhesive material 42 may be formed at the end portions 72 to enhance the bond to the surface of the balloon 16 proximate the ends of the cutting member 20 to assure the end portions 72 do not debond from the balloon 16 and lift away from the surface of the balloon 16. The enlarged foot 74 may have a width W4 greater than the width W3 of the base 43 throughout the intermediate portion 70 of the subassembly, thus increasing the bonding area of the second polymeric adhesive material 42 to the surface of the balloon 16 proximate the end portions 72.

Figure 7:
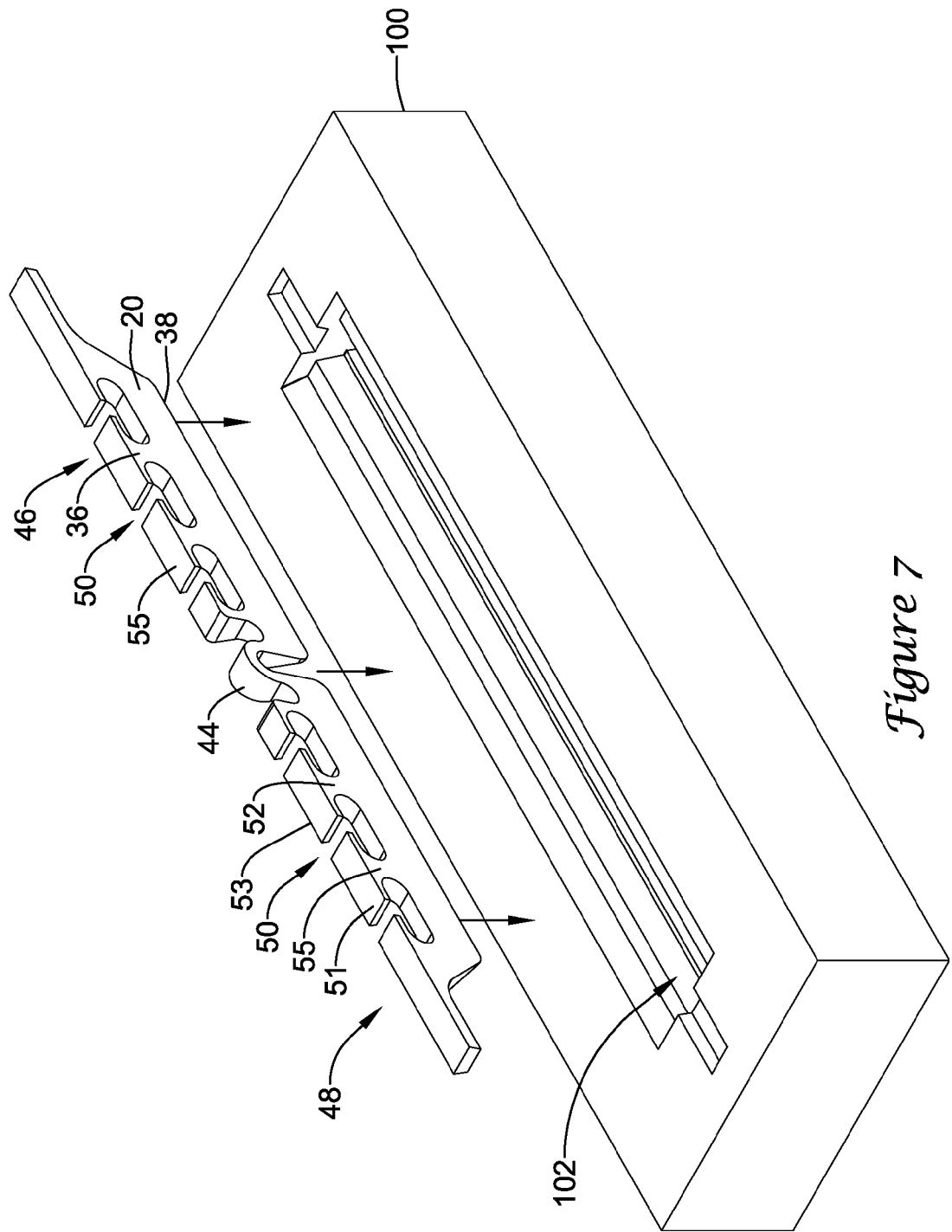
FIGS. 7-12 illustrate an exemplary method of mounting a cutting element to a balloon of a balloon catheter.

An exemplary method of mounting a cutting member 20 to a balloon 16 of a balloon catheter 10 will now be described with reference to FIGS. 7-12. As shown in FIG. 7, a cutting member 20 may be positioned in a mold 100 having a cavity 102 formed therein. In some instances, the mold 100 may be formed of a transparent or translucent silicone material, allowing ultraviolet light to travel through the mold 100. The cutting member 20 may be positioned with the cutting edge 38 facing into the mold 100 with the base portion 36 exposed in the cavity 102.

Some of the other features of the cutting member 20 may also be seen in FIG. 7. For example, the base portion 36 of the cutting member 20 may include series of alternating tabs 55 and openings 50 extending along the base portion 36 of the cutting member 20. The plurality of openings 50 may extend through the base portion 36 from the first side surface 52 to the second side surface 53 of the cutting member 20. The openings 50 may open out to the lower surface 51 of the cutting member 20 in some instances. The shape of the tabs 55 and openings 50 may vary. For example, in some instances the tabs 55 may have a shape similar to an inverted T-shape when viewed from the side or otherwise have a splayed pillar-like shape such that the portion of the openings 50 opening out to the lower surface 51 is narrower than another portion of the openings 50 closer to the cutting edge 38. In other words, the width (in the longitudinal direction) of the tabs 55 may be greater at or proximate the lower surface 51 of the cutting member 20 than at a location closer to the cutting edge 38.

In addition to providing the cutting member 20 with a degree of lateral flexibility, the openings 50 between the tabs 55 may provide a location for the first polymeric adhesive material 41 to flow into as the base portion 36 of the cutting member 20 is embedded into the first polymeric adhesive material 41 during the molding process. Thus, the first polymeric adhesive material 41 may encapsulate the base portion 36, including the tabs 55 and extend through the openings 50 to mechanically interlock the base portion 36 of the cutting member 20 in the mounting pad 40 to enhance the securement of the cutting member 20 in the mounting pad 40.

The viscosity of the first polymeric adhesive material 41 may be chosen in the range of about 1,000 cP to about 15,000 cP, about 5,000 cP to about 10,000 cP, or about 6,000 cP to about 7,000 cP at room temperature. A viscosity in this range may permit the first polymeric adhesive material 41 to flow into the openings 50 while addressing other considerations. Polymeric adhesive materials having low viscosities may have a tendency of lifting the cutting member 20 out of the mold 100 during the molding process, whereas polymeric adhesive materials having high viscosities may inhibit the ability to dispose the polymeric adhesive material in the openings 50 without excessive air entrainment.

Figure 8:
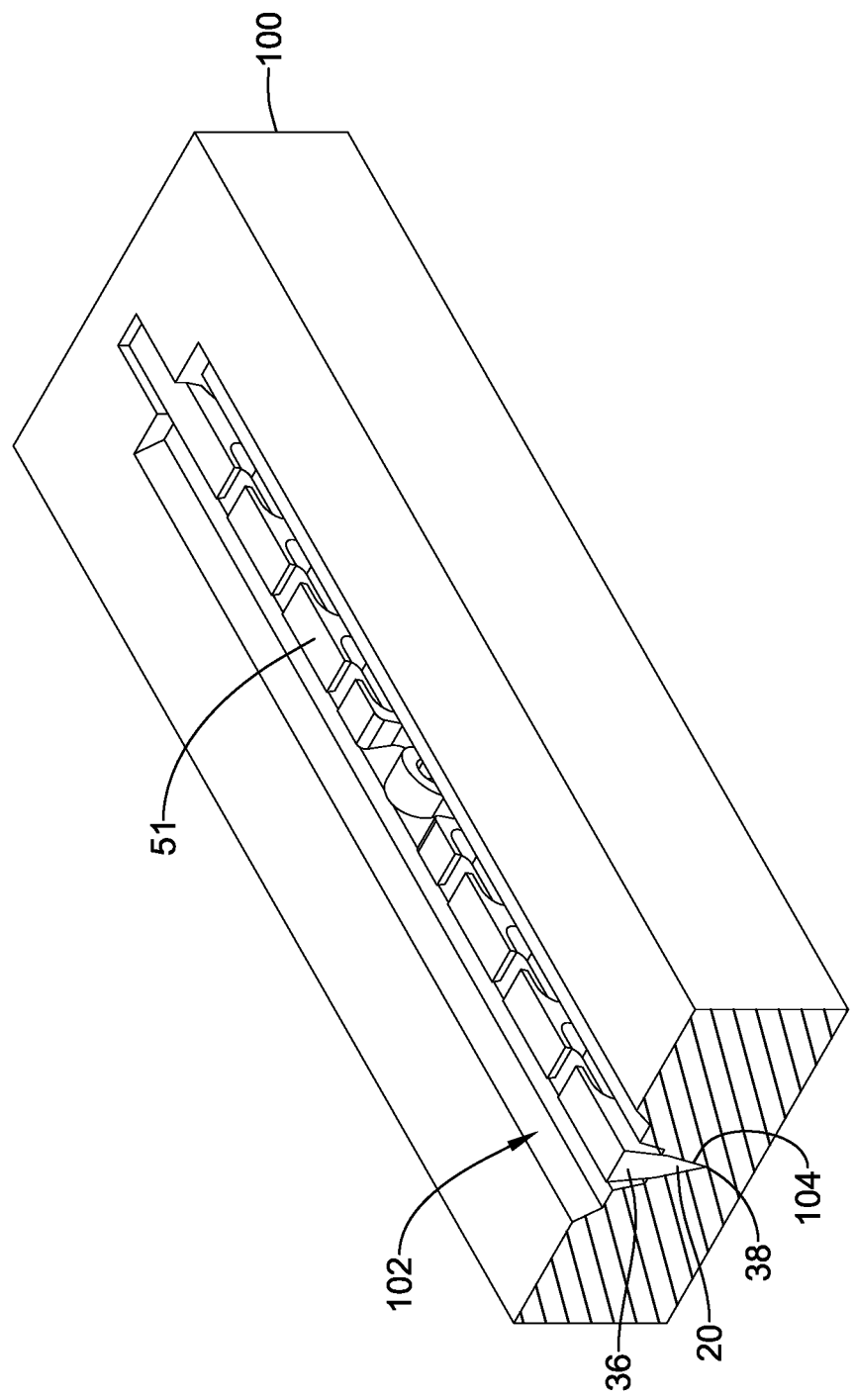

FIG. 8 is a cut-away perspective view of the cutting member 20 positioned in the mold 100 prior to encapsulating the base portion 36 in the mounting pad 40. The cutting edge 38 of the cutting member 20 may extend into a slit 104 in the mold 100 to hold the cutting member 20 in an inverted position with the base portion 36 facing upward. As can be seen from the cross-section shown in FIG. 8, the shape of the cavity 102 may correspond to the shape of the mounting pad 40 to be cast around the base portion 36 of the cutting member 20. The lower surface 51 of the cutting member 20 (facing upward) may be positioned lower than the upper surface of the mold 100 such that a layer of the first polymeric adhesive material 41 may be formed across the lower surface 51, or the lower surface 51 of the cutting member 20 may be positioned flush with the upper surface of the mold 100.

The cutting member 20, positioned in the mold 100, may then be placed in an oven and heated to an elevated temperature. For example, the cutting member 20 and mold 100 may be placed in an oven heated to about 30° C., about 40° C., or about 50° C., for 30 minutes or more.

Figure 9:
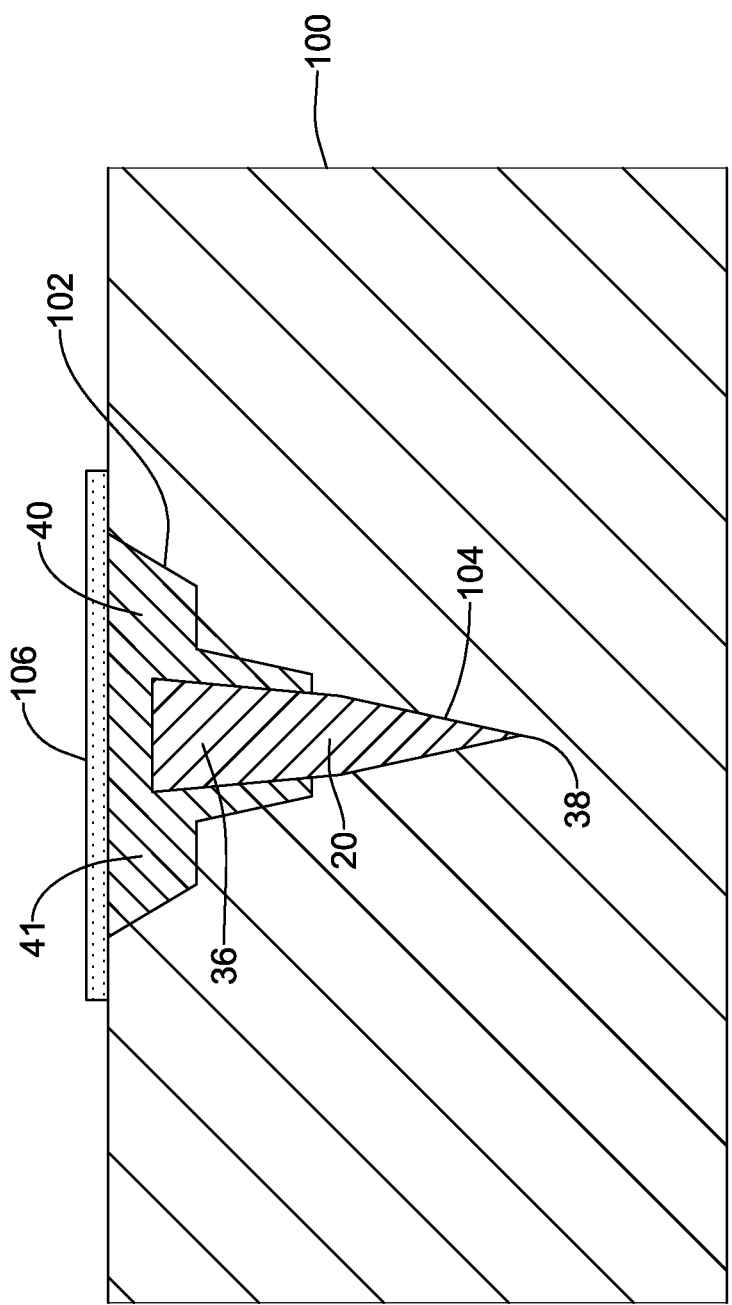

With the cutting member 20 heated to an elevated temperature, the first polymeric adhesive material 41 may be applied with an applicator in the cavity 102 adjacent the base portion 36 of the cutting member 20. The first polymeric adhesive material 41 may be disposed in the cavity 102 on each side of the cutting member 20 and forced through the openings 50 in the base portion 36 to fill or substantially fill the cavity 102. The cross-sectional view of FIG. 9 illustrates the cavity 102 filled with the first polymeric adhesive material 41 to cast the mounting pad 40 around the base portion 36 of the cutting member 20. Once the cavity 102 has been filled with the first polymeric adhesive material 41, a film 106, such as a transparent silicone film, may be placed over the cavity 102.

The first polymeric adhesive material 41 may then be cured to cast the mounting pad 40 onto the base portion 36 of the cutting member 20. For example, if the first polymeric adhesive material 41 is a UV curable adhesive, the first polymeric adhesive material 41 may be exposed to ultraviolet light to initiate polymerization and cure the first polymeric adhesive material 41. To cure the first polymeric adhesive material 41, the mold 100, with the first polymeric adhesive material 41 disposed in the cavity 102 around the base portion 36 of the cutting member 20, may be passed through an exposure tunnel 110, such as a Loctite® Zeta 7610 exposure tunnel, shown in FIGS. 10A-10C. One or more passes may be made to cure the first polymeric adhesive material 41. The speed of the conveyor 112 may be set to expose the first polymeric adhesive material 41 to ultraviolet light for a desired duration of time per pass. For example, the speed of the conveyor 112 of the exposure tunnel 110 may be set to expose the first polymeric adhesive material 41 to ultraviolet light for 60 seconds, 70 seconds, 80 seconds, or 90 seconds per pass in some instances.

Figure 10C:
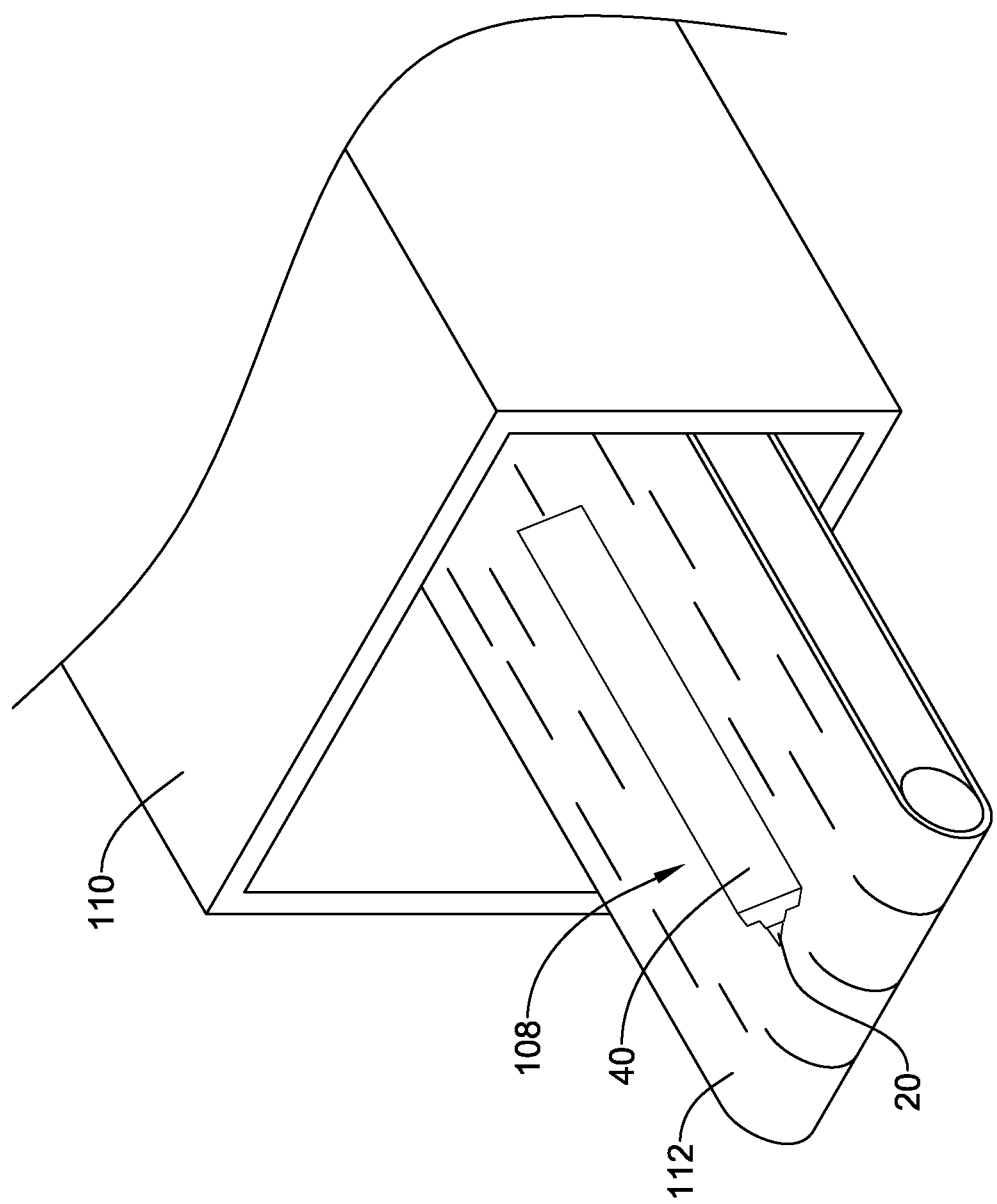

The mold 100, with the first polymeric adhesive material 41 disposed in the cavity 102 around the base portion 36 of the cutting member 20, may be passed through the exposure tunnel 110 during a first pass with the base portion 36 of the cutting member 20 facing upward, and thus the cutting edge 38 facing downward, as shown in FIG. 10A. The cast blade 108 (i.e., the mounting pad 40 with the cutting member 20 encased therein) may then be removed from the mold 100, with the film 106 retained with the cast blade 108. The cast blade 108 may then be rotated such that the cast blade 108 is setting on the film 106 with the cutting edge 38 of the cutting member 20 facing upward. The cast blade 108 may then be passed through the exposure tunnel 110 for a second pass with the base portion 36 of the cutting member 20 facing downward and the cutting edge 38 facing upward, as shown in FIG. 10B. The speed of the conveyor 112 of the exposure tunnel 110 may be set at the same speed as the first pass, or the speed may be changed. The film 106 may then be removed from the cast blade 108 and the exposure process may be repeated again. For example, the cast blade 108 may then be passed through the exposure tunnel 110 for a third pass with the base portion 36 of the cutting member 20 facing upward and the cutting edge 38 facing downward, as shown in FIG. 10C. The speed of the conveyor 112 of the exposure tunnel 110 may be set at the same speed as the first and/or second pass, or the speed may be changed.

In some instances, the cutting member 20 may include a bridge 44 coupling a first segment 46 of the cutting member 20 with a second segment 48 of the cutting member 20, as shown in FIG. 7. The bridge 44 may be configured to fracture, separating the first segment 46 from the second segment 48 to increase the flexibility of the cutting member 20, as described in U.S. Pat. No. 7,291,158, incorporated by reference herein. The fractured portion of the bridge 44 may be embedded in the mounting pad 40, shielding tissue from unintentional damage from contact with the fractured portions. The bridge 44 may be fractured prior to use or during the use of the cutting balloon catheter 10 in a medical procedure. In some instances, the bridge 44 may be fractured prior to mounting the cast blade 108 onto the balloon 16.

It may be desirable that the first polymeric adhesive material 41 has a percent elongation at break of 5% or more to ensure the first polymeric adhesive material 41 has sufficient ductility to accommodate stretching of the mounting pad 40 as the first segment 46 is bent relative to the second segment 48 to fracture the bridge 44. Polymeric adhesive materials having an elongation at break of less than 5% may not be sufficiently ductile, thus portions of the polymeric adhesive material may break away from the tabs 55 and openings 50 of the base portion 36 of the cutting members 20 as the first segment 46 is bent relative to the second segment 48.

Figure 11:
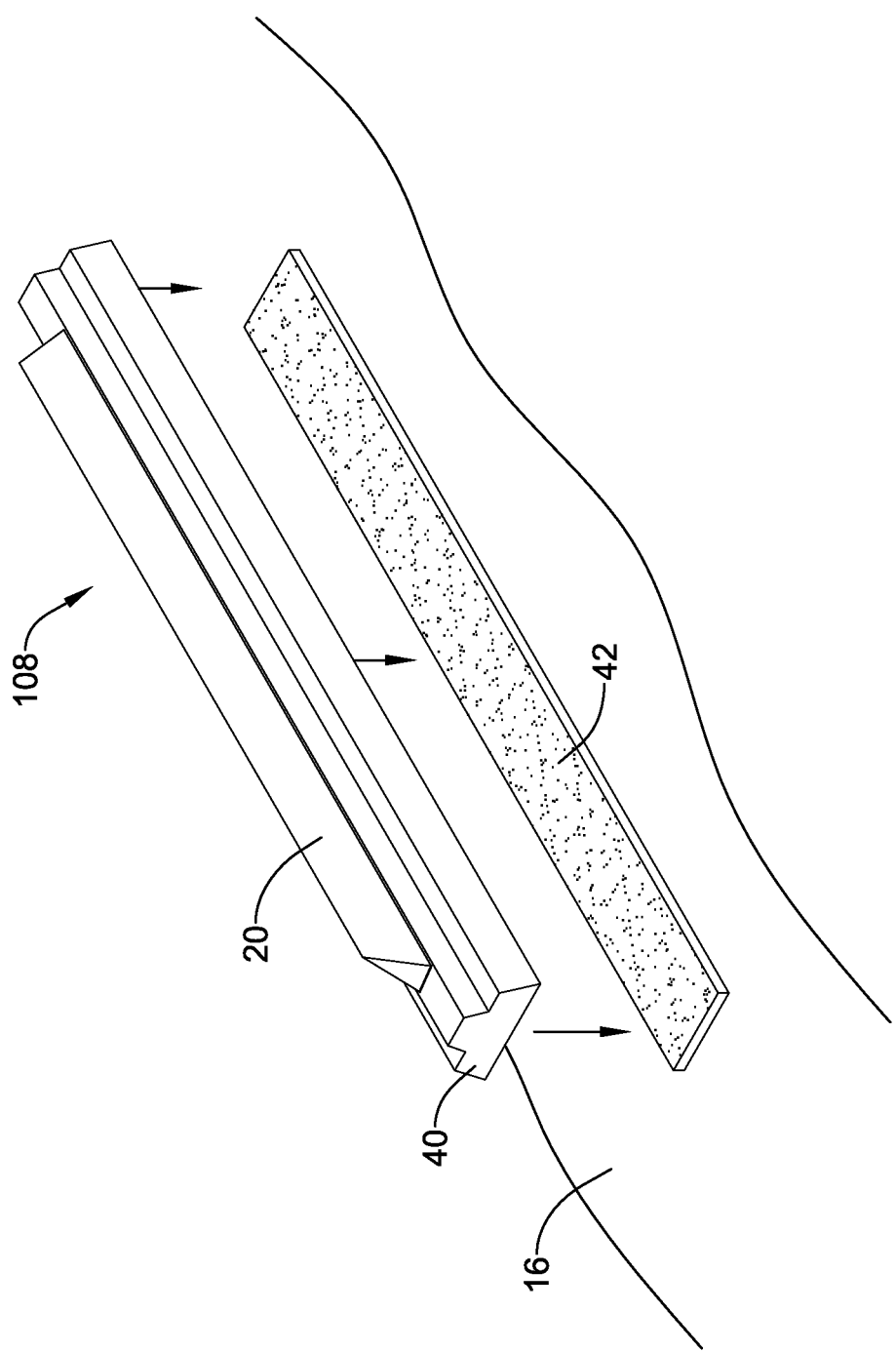

After the first polymeric adhesive material 41 has cured to cast the cutting member 20 in the mounting pad 40, the cast blade 108 may be adhesively bonded to the exterior surface of the balloon 16 with the second polymeric adhesive material 42. For example, the balloon 16 may be placed in a fixture and inflated to a desired mounting pressure, such as about 60 psi, about 80 psi, or about 100 psi. The second polymeric adhesive material 42 may be stamped onto the surface of the balloon 16 in longitudinal strips, as shown in FIG. 11, and then the cast blade 108 may be mounted thereto by pressing the mounting pad 40 into the strip of the second polymeric adhesive material 42. In other embodiments, the second polymeric adhesive material 42 may first be applied to the mounting pad 40, and then the cast blade 108, with the second polymeric adhesive material 42 applied thereto, may be adhered to the exterior surface of the balloon 16. The mounting step may be repeated for each cast blade 108 until the balloon 16 is fully populated with the desired number of cutting members 20.

Figure 12:
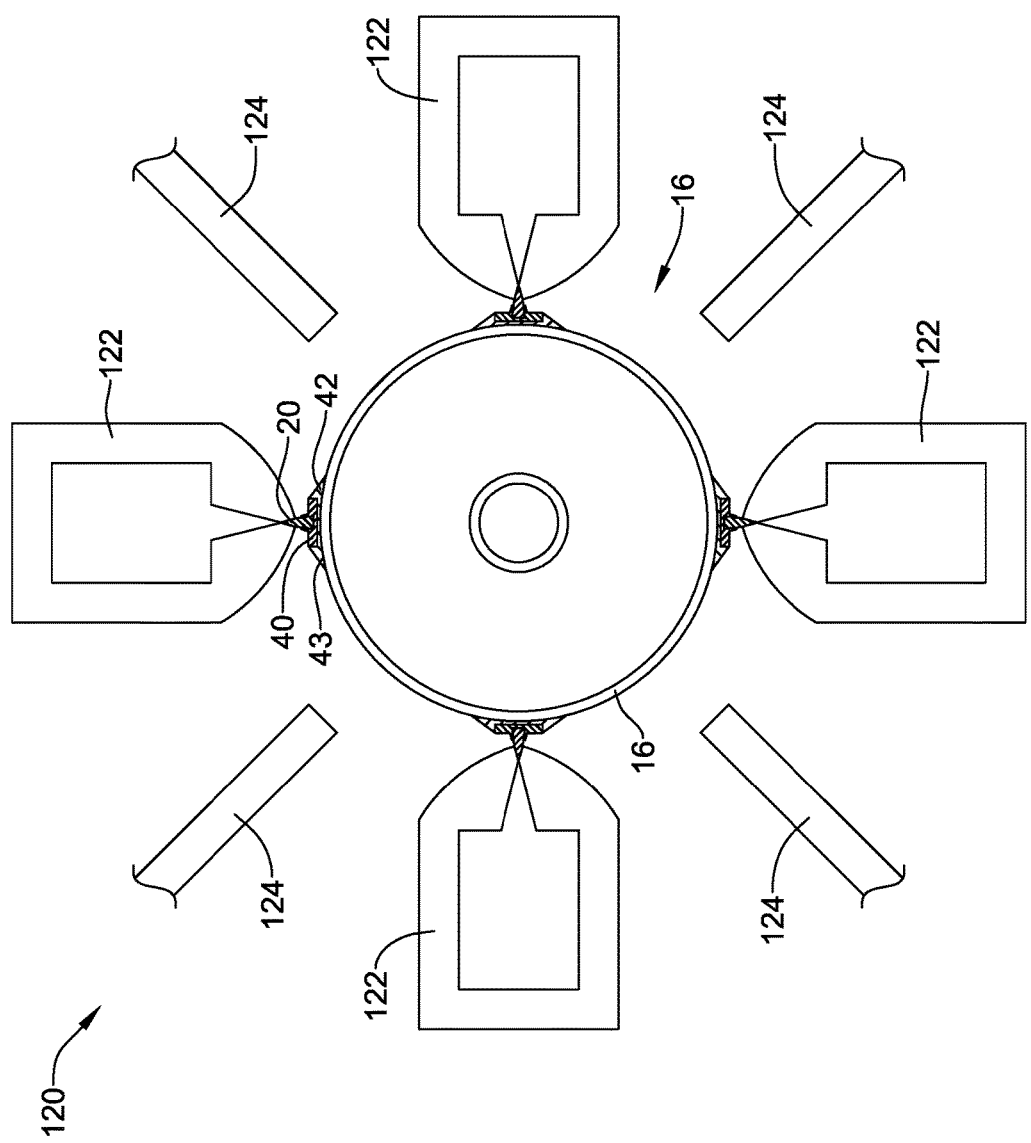

As shown in FIG. 12, with the cutting members 20 held in place with supports 122 of a mounting fixture 120, the second polymeric adhesive material 42, forming the base 43, may be cured to mount the cast blade 108 onto the balloon 16. For example, if the second polymeric adhesive material 42 is a UV curable adhesive, the second polymeric adhesive material 42 may be exposed to ultraviolet light to initiate polymerization and cure the second polymeric adhesive material 42. To cure the second polymeric adhesive material 42, the mounting fixture 120, with the second polymeric adhesive material 42 applied to the balloon 16 and cast blades 108 positioned thereon, may be subjected to a source of ultraviolet light. For example, UV wands 124, such as Loctite® Zeta 7735 exposure wands, may be positioned proximate the second polymeric adhesive material 42 and activated for a desired duration of time, such as about 1 minute, about 2 minutes, or about 3 minutes. In some instances, the mounting fixture 120 may be rotated, such as at a speed of about 10 RPM to about 35 RPM, during the exposure process. Additionally, nitrogen may be discharged toward the second polymeric adhesive material 42 during the exposure process to reduce the oxygen inhibition effect.

The balloon 16, with the cutting members 20 mounted thereon, may then be removed from the mounting fixture 120. The balloon 16, with the cutting members 20 mounted thereon, may then passed through the exposure tunnel 110 to further expose the first and second polymeric adhesive materials 41, 42, if desired. For example, the subassembly may be passed through the exposure tunnel 110 for one or more additional passes to expose the first and second polymeric adhesive materials 41, 42 to ultraviolet light for about 25 seconds, 30 seconds, or 35 seconds per pass. The subassembly may be rotated between passes to ensure all portions are exposed to the ultraviolet light.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of securing a cutting blade to a balloon of a balloon catheter, the method comprising:
    placing a cutting blade in a mold having a cavity;
    molding a mounting pad formed of a first polymeric adhesive material about a base portion of the cutting blade by:
        injecting the first polymeric adhesive material in the cavity of the mold around the base portion of the cutting blade, such that the base portion of the cutting blade is encased in the first polymeric adhesive material; and
        curing the first polymeric adhesive material to form the mounting pad around the base portion of the cutting blade;
    wherein the mounting pad includes a lower portion having a lower surface, an opposing upper surface, and a thickness measured between the lower surface and the upper surface, and wherein the mounting pad includes a projecting portion extending from the upper surface of the lower portion on opposite sides of the base portion of the cutting blade, the projecting portion having opposing side surfaces intersecting the upper surface of the lower portion of the mounting pad; and
    adhering the lower surface of the mounting pad, with the base portion of the cutting blade encased therein, to a surface of a balloon with a second polymeric adhesive material;
    wherein the balloon has a longitudinal axis, wherein a portion of the second polymeric adhesive material is located radially outward of the first polymeric adhesive material such that an imaginary line extending radially outward from the longitudinal axis passes through both the first polymeric adhesive material and the portion of the second polymeric adhesive material located radially outward of the first polymeric adhesive material.

2. The method of claim 1, wherein the curing step comprises:
    exposing the first polymeric adhesive material to ultraviolet light while in the mold.

3. The method of claim 2, wherein the curing step comprises:
    passing the mold with the cutting blade positioned therein and the first polymeric adhesive material in the cavity of the mold through an exposure tunnel for a first pass.

4. The method of claim 3, wherein the curing step comprises:
    removing the cutting blade and the mounting pad from the mold; and then
    passing the cutting blade and the mounting pad through the exposure tunnel for a second pass.

5. The method of claim 1, wherein the cutting blade is placed in the mold such that the base portion of the cutting blade is facing upward and positioned in the cavity.

6. The method of claim 1, wherein the adhering step comprises:
    applying the second polymeric adhesive material to the surface of the balloon, then;
    bringing the mounting pad, with the base portion of the cutting blade encased therein, into contact with the second polymeric adhesive material applied to the surface of the balloon.

7. A method of securing a cutting blade to a balloon of a balloon catheter, the method comprising,
    Applying a first polymeric adhesive material about a base portion of a cutting blade, such that the base portion of the cutting blade is encased in the first polymeric adhesive material;
    Exposing the first polymeric adhesive material to ultraviolet energy, with the base portion of the cutting blade encased therein, to cure the first polymeric adhesive material to form a mounting pad surrounding the base portion of the cutting blade;
    Adhering the mounting pad, with the base portion of the cutting blade encased therein, to a surface of a balloon with a second polymeric adhesive material; and
    Exposing the second polymeric adhesive material to ultraviolet energy to cure the second polymeric adhesive material to mount the cutting blade onto the balloon;
    Wherein the balloon has a longitudinal axis, wherein a portion of a the second polymeric adhesive material is located radially outward of the first polymeric adhesive material such that an imaginary line extending radially outward from the longitudinal axis passes through both the first polymeric adhesive material and the portion of the second polymeric adhesive material located radially outward of the first polymeric adhesive material, and wherein the first polymeric adhesive material is different than the second polymeric adhesive material.

8. A method of securing a cutting blade to a balloon of a balloon catheter, the method comprising:
applying a first polymeric adhesive material about a base portion of a cutting blade, such that base portion of the cutting blade is encased in the first polymeric adhesive material;
exposing the first polymeric adhesive material to ultraviolet energy, with the base portion of the cutting blade encased therein, to cure the first polymeric adhesive material to form a mounting pad surrounding the base portion of the cutting blade;
holding the cutting blade, with the base portion of the cutting blade encased in the mounting pad, and an inflated balloon in a support of a mounting fixture;
applying a second polymeric adhesive material to one of the mounting pad and the inflated balloon;
mounting the cutting blade, with the second polymeric adhesive material interposed between the mounting pad and the inflated balloon, to the inflated balloon while the cutting blade is held by the support and the inflated balloon is positioned in the mounting fixture; and
exposing the second polymeric adhesive material to ultraviolet energy to cure the second polymeric adhesive material while the cutting blade is held by the support of the mounting fixture;
wherein the balloon has a longitudinal axis, wherein a portion of the second polymeric adhesive material is located radially outward of the first polymeric adhesive material such that an imaginary line extending radially outward from the longitudinal axis passes through both the first polymeric adhesive material and the portion of the second polymeric adhesive material located radially outward of the first polymeric adhesive material.

9. The method of claim 8, wherein the second polymeric adhesive material is applied to a surface of the balloon prior to bringing the mounting pad, with the base portion of the cutting blade encased therein, into contact with the second polymeric adhesive material.

10. The method of claim 8, wherein the second polymeric adhesive material is applied to the mounting pad prior to bringing the second polymeric adhesive material into contact with a surface of the balloon.

11. The method of claim 8, wherein the step of exposing the second polymeric adhesive material to ultraviolet energy includes positioning one or more ultraviolet (UV) wands proximate the second polymeric adhesive material and activating the one or more ultraviolet (UV) wands for a duration of time.

12. The method of claim 11, wherein the one or more ultraviolet (UV) wands are positioned proximate the second polymeric adhesive material while the cutting blade and the balloon are positioned in the mounting fixture.

13. The method of claim 8, wherein the step of exposing the first polymeric adhesive material to ultraviolet energy includes passing the first polymeric adhesive material, with the base portion of the cutting blade encased therein, through an exposure tunnel.

* * * * *